(12) United States Patent
Mickle et al.

(10) Patent No.: US 9,700,234 B2
(45) Date of Patent: Jul. 11, 2017

(54) SYSTEM AND METHOD FOR STORING INFORMATION RELATING TO A MEDICAL IMPLANT DEVICE

(71) Applicant: UNIVERSITY OF PITTSBURGH-OF THE COMMONWEALTH SYSTEM OF HIGHER EDUCATION, Pittsburgh, PA (US)

(72) Inventors: Marlin H. Mickle, Pittsburgh, PA (US); John Lee Berger, Franklin Lakes, NJ (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 427 days.

(21) Appl. No.: 14/490,773

(22) Filed: Sep. 19, 2014

(65) Prior Publication Data

US 2015/0094547 A1 Apr. 2, 2015

Related U.S. Application Data

(60) Provisional application No. 61/884,362, filed on Sep. 30, 2013.

(51) Int. Cl.
| | | |
|---|---|---|
| G06K 9/00 | (2006.01) | |
| A61B 5/07 | (2006.01) | |
| A61B 5/00 | (2006.01) | |
| A61B 90/90 | (2016.01) | |
| A61B 90/98 | (2016.01) | |
| G06F 19/00 | (2011.01) | |

(52) U.S. Cl.
CPC ............ *A61B 5/076* (2013.01); *A61B 5/4851* (2013.01); *A61B 90/90* (2016.02); *A61B 90/98* (2016.02); *A61B 5/686* (2013.01); *G06F 19/322* (2013.01)

(58) Field of Classification Search
CPC ..... G06F 19/322; A61B 5/4851; A61B 90/98; A61B 5/076; A61B 90/90; A61B 5/686
USPC ........................................................ 382/128
See application file for complete search history.

(56) References Cited

U.S. PATENT DOCUMENTS

| | | |
|---|---|---|
| 6,487,844 B1 | 12/2002 | Lohn et al. |
| 7,228,183 B2 | 6/2007 | Sun et al. |
| 7,333,013 B2 | 2/2008 | Berger |
| 7,825,807 B2 | 11/2010 | Mickle et al. |
| 7,932,825 B2 | 4/2011 | Berger |
| 2005/0010300 A1* | 1/2005 | Disilvestro ............ A61B 90/98 623/18.12 |

(Continued)

*Primary Examiner* — Gregory F Cunningham
(74) *Attorney, Agent, or Firm* — Eckert Seamans Cherin & Mellott, LLC; Philip E. Levy (57) ABSTRACT

A method of storing information relating, to a medical implant device having a number of implant elements includes receiving a first image, the first image showing a surgical site and the medical implant device, creating a second image using the first image and a stored list of possible implant elements, the second image showing the surgical site and the medical implant device with a number of labels associated therewith, wherein each of the labels is associated with a respective one of the implant elements and indicates one of the possible implant. elements from the stored list, and storing the second image on an transponder device structured to be attached to the medical implant device or at a medically appropriate site on or within a patient's body.

28 Claims, 7 Drawing Sheets

(56) References Cited

U.S. PATENT DOCUMENTS

| | | | |
|---|---|---|---|
| 2006/0232408 A1* | 10/2006 | Nycz | A61B 90/98 |
| | | | 340/572.1 |
| 2007/0238984 A1* | 10/2007 | Maschke | A61B 5/0031 |
| | | | 600/424 |
| 2013/0105577 A1* | 5/2013 | Hildreth | A61B 17/7001 |
| | | | 235/385 |
| 2014/0263674 A1* | 9/2014 | Cerveny | G06K 19/06028 |
| | | | 235/494 |

* cited by examiner

SYSTEM AND METHOD FOR STORING INFORMATION RELATING TO A MEDICAL IMPLANT DEVICE

CROSS-REFERENCE TO RELATED APPLICATIONS

This application claims priority under 35 U.S.C. §119(e) from U.S. provisional patent application No. 61/884,362, entitled "System and Method for Storing Information Relating to a Medical Implant Device" and filed on Sep. 30, 2013, the contents of which are incorporated herein by reference.

BACKGROUND OF THE INVENTION

1. Field of the Invention

The present invention pertains to medical implant devices, such as orthopedic implants, cardiac implants, dental implants, general surgical implants, neurological implants, gastrointestinal implants, urological implants, gynecological implants, or some other implantable medical device, and, in particular, to a system and method for storing information on or in the proximity of a medical implant device that identifies the particular elements/parts of the medical implant device.

2. Description of the Related Art

U.S. Pat. Nos. 7,333,013 and 7,932,825 describe a system wherein a medical implant device, such as, without limitation, an orthopedic (e.g., an artificial knee or hip), a cardiac implant (e.g., a pacemaker), or some other implantable medical device has a radio frequency identification (RFID) tag mounted thereto or in the proximity thereof so as to be implanted in the patient's body. The RFID tag stores information relating to the implant and/or the patient, such as, without limitation, the implant type/model/serial number, the implant manufacturer, the procedure date, the hospital and/or the implanting surgeon. That information may later be obtained from outside of the patient's body when needed by reading the RFID tag using a properly equipped RFID reader device. For example, that information can be read by the surgeon or another healthcare professional during, a post operative or later visit in order to obtain information needed by that individual during the visit in order to properly examine and treat the patient. As another example, that information can also be read and transmitted to a secure patient database for use in medical outcomes research performed by, for example, a healthcare organization or implant manufacturer.

In one particular implementation, described in U.S. Pat. Nos. 7,333,013 and 7,932,825, the RFID tag mounted to the implant is a passive RFID tag that includes an antenna, and may be read using a conventional RFID reader that is structured to read the implanted passive RFID tag over an air interface, in another particular implementation, an alternative RFID reader may be used, wherein the RFID reader is structured and configured to read the implanted RFID tag: by making, a direct (i.e., non-air interface) electrical connection to the RFID tag through the patient's living tissue using a probe provided as part of the RFID reader device (i.e., using transcutaneous contact, transcutaneous near field communication (TNFC), and other communication technologies). A TNFC implementation is described in U.S. Pat. Nos. 6,487,844, 7,228,183 and 7,825,807.

In certain medical implant applications, such as, without limitation, orthopedic trauma applications, many different elements or parts from various vendor kits may be placed in the patient to form the medical implant device. For example, medical implant device may comprise a plate or rod from a first vendor, a number of screws from a second vendor and a number of screws from a third vendor. The ability to later identify the various different elements or parts in the medical implant device can be important, such as when follow up care for the patient to, for example, repair or replace a part of the medical implant device, is necessary. A paper trail of the different elements or parts of the medical implant device is difficult to maintain for the patient due to a variety of reasons including, for example, the urgency of the procedure when performed, the patient living in geographic area other than where the procedure was performed, and/or an unclear insurance profile. As a result, at a later time when one or more of the various elements of the medical implant device need to be adjusted, repaired or replaced, to overcome this frequent lack of proper documentation, the surgeon must have available all of the possible kits which could have been used for the original procedure to ensure that he or she has what is then needed.

SUMMARY OF THE INVENTION

In one embodiment, a method of storing information relating to a medical implant device having a number of implant elements is provided. The method includes receiving a first image, the first image showing a surgical site and the medical implant device, creating a second image using the first image and a stored list of possible implant elements, the second image showing the surgical site and the medical implant device with a number of labels associated therewith, wherein each of the labels is associated with a respective one of the implant elements and indicates one of the possible implant elements from the stored list, and storing the second image on a transponder device structured to be attached to the medical implant device or at a medically appropriate site on or within a patient's body.

In another embodiment, a computer program product including a computer usable medium having a computer readable program code embodied therein is provided, wherein the computer readable program code has a number of routines adapted to be executed to implement the method just described above.

In still another embodiment, a system for storing information relating to a medical implant device having a number of implant elements is provided. The system includes an image receiving component structured and configured for receiving a first image, the first image showing a surgical site and the medical implant device, a storage component structured and configured for storing a stored list of possible implant elements, an image creating component structured and configured for creating a second image using the first image and the stored list of possible implant elements, the second image showing the surgical site and the medical implant device with a number of labels associated therewith, wherein each of the labels is associated with a respective one of the implant elements and indicates one of the possible implant elements from the stored list, and a transponder storage component structured and configured for storing the second image on a transponder device structured to be attached to the medical implant device or at a medically appropriate site on or within a patient's body.

DETAILED DESCRIPTION OF EXEMPLARY EMBODIMENTS

As used herein, the singular form of "a", "an", and "the" include plural references unless the context clearly dictates otherwise. As used herein, the statement that two or more parts or elements are "coupled" shall mean that the parts are joined or operate together either directly or indirectly, i.e., through one or more intermediate parts or elements, so long as a link occurs.

As used herein, "directly coupled" means that two elements are directly in contact with each other.

As used herein, "fixedly coupled" or "fixed" means that two elements are coupled so as to move as one while maintaining, a constant orientation relative to each other.

As used herein, the word "unitary" means a part is created as a single piece or unit. That is, a part that includes pieces that are created separately and then coupled together as a unit is not a "unitary" part or body.

As employed herein, the statement that two or more parts or elements "engage" one another shall mean that the parts exert a force against one another either directly or through one or more intermediate parts or elements.

As employed herein, the term "number" shall mean one or an integer greater than one (i.e., a plurality).

As used herein, the terms "component" and "system" as used in the computer context are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described with respect to certain figures or graphs as screenshots, those skilled in the relevant art will recognize that various other alternatives can be employed. The terms "screen," "web page," and "page" are generally used interchangeably herein. The pages or screens are stored and/or transmitted as display descriptions, as graphical user interfaces, or by other methods of depicting information on a screen (whether personal computer, PDA, mobile telephone, or other suitable device, for example) where the layout and information or content to be displayed on the page is stored in memory, database, or another storage facility.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention will now be described, for purposes of explanation, in connection with numerous specific details in order to provide a thorough understanding of the subject invention. It will be evident, however, that the present invention can be practiced without these specific details without departing from the spirit and scope of this innovation.

Figure 1:
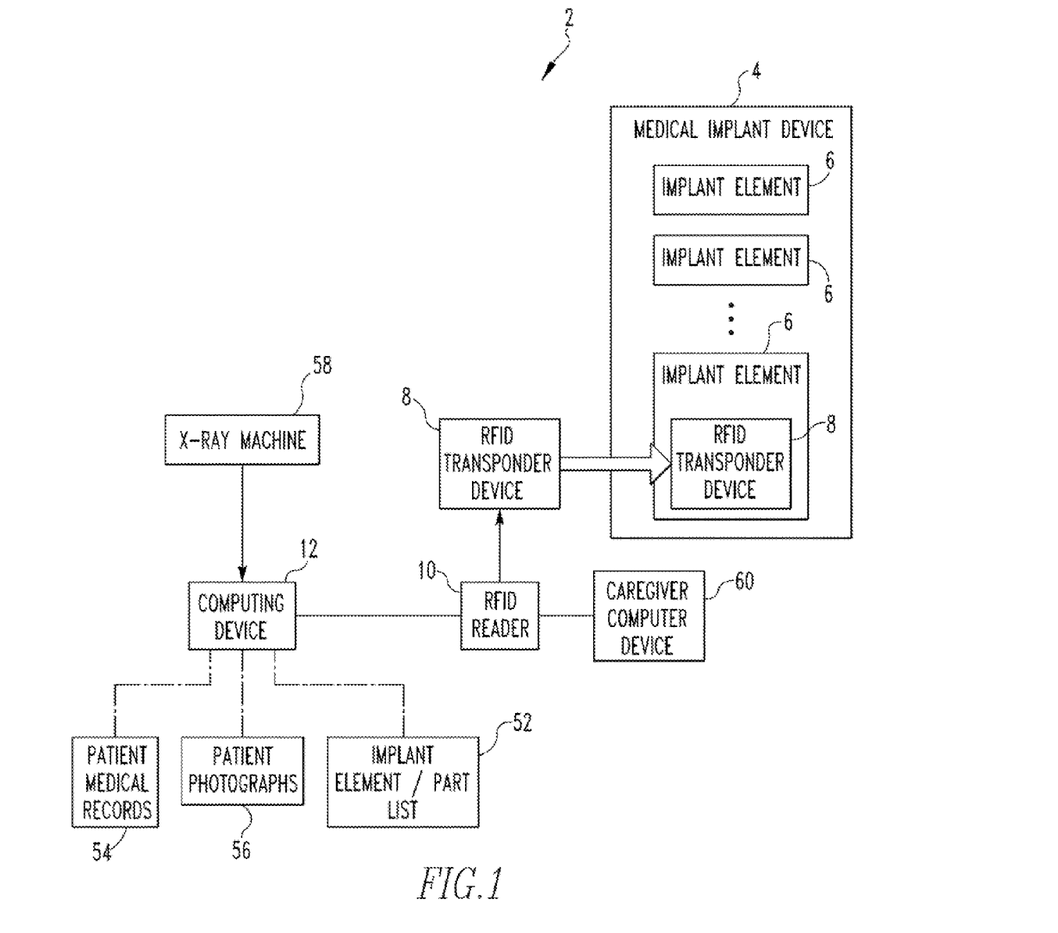
FIG. 1 is a schematic diagram of a system for storing information on a medical implant device that identifies the particular elements or parts of the medical implant device according to an exemplary embodiment of the present invention.

FIG. 1 is a schematic diagram of a system 2 for storing information on a medical implant device that identifies the particular elements or parts of the medical implant device according to an exemplary embodiment of the present invention. System 2 includes medical implant device 4 which may be, for example and without limitation, an orthopedic implant, a cardiac implant, a dental implant, a general surgical implant, a neurological implant, a gastrointestinal implant, a urological implant, a gynecological implant, or some other implantable medical device. In the illustrated, exemplary embodiment, medical implant device 4 is an orthopedic implant having a number of implant elements 6 that together form the medical implant device 4. For example, and without limitation, medical implant device 4 may an orthopedic implant having a number of plates and screws for treating a fractured bone.

System 2 also includes an RFID transponder device 8 that may, in various embodiments, be a passive or active RFID tag device. In the exemplary embodiment, as described in detail herein, MID transponder device 8 is structured and configured to store certain information relating to the patient and medical implant device 4, including an identification of the implant elements 6 making up medical implant device 4, and, in the exemplary embodiment, is structured to be fixedly coupled to one of the implant elements 6 making up medical implant device 4 (as shown schematically in FIG. 1). In another, alternative embodiment, RFID transponder device 8 may be implanted and attached to the patient's body in a medically appropriate manner so as to provide all information and functionality as if it had been attached to medical implant device 4. In still another, alternative embodiment. RFID transponder device 8 may be attached on the patient's body (i.e., outside the body). and may be embedded into various objects such as clothing, a bandage, a watch, a bracelet, glasses, issue, a brace, or anything that can be worn on or embedded on the body. In addition. REID transponder device 8 is structured and configured to be read by an RFID reader device 10 forming part of system 2 so that the information stored by RFID transponder device 8 (as described herein) may be readily accessed by, for example, a caregiver of the patient (e.g., a surgeon) performing follow up care for the patient.

In the illustrated exemplary, non-limiting embodiment, REID transponder device 8 is a passive RFID transponder device (e.g., a passive RFID tag) that may be read using a touch probe type RFID reader device 10 that is structured and configured to read the implanted RFID transponder device 8 by making, a direct (i.e., non-air interface) electrical connection to RFID transponder device 8 through the living tissue of the patient using a probe provided as part of touch probe RFID reader device 10 using transcutaneous contact and transcutaneous near field communication (TNFC) or transcutaneous far field communication (TFFC)).

Figure 2:
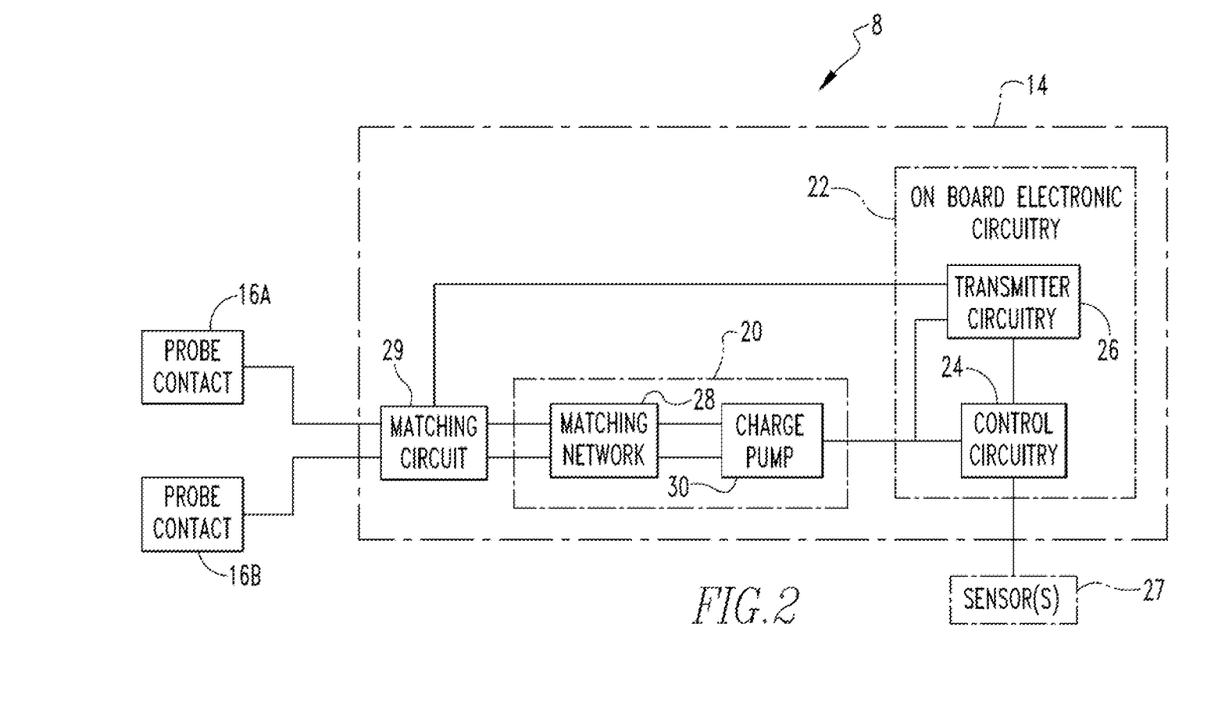
FIG. 2 is a schematic representation of an RFID transponder device according to one particular, non-limiting exemplary embodiment. that may be used in the system of FIG. 1.

As described above, in the exemplary embodiment, RFID transponder device 8 is a passive device powered by the RF signal sent by touch probe type RFID reader device 10. One passive tag technology, known as backscatter technology, generates signals by backscattering the carrier signal sent from the RFID reader. In another technology, described in U.S. Pat. Nos. 6,289,237, 6,615,074, 6,856,291, 7,057,514, and 7,084,605 (and commonly referred to as energy harvesting). RF energy from the REID reader is harvested and converted to a DC voltage by an antenna/matching circuit/ charge pump combination. The DC voltage is then used to power the circuitry that transmits information to the RED reader at, for example, a different frequency, FIG. 2 is a schematic representation of RFID transponder device 8 according to one particular, non-limiting exemplary embodiment wherein passive technology in the form of energy harvesting as just described is employed to power the electronic components of REID transponder device 8. RFID transponder device 8 includes an integrated circuit chip 14 operatively coupled to probe contacts 16A and 16B in the form of interfacing conductors, the function of which is described herein. In addition, as seen in FIG. 2, integrated circuit chip 14 includes energy harvesting circuitry 20, on-board electronic circuitry 22, and a matching circuit 29. Matching circuit 29 is operatively coupled to probe contacts 16A and 16B at an input end thereof to match integrated circuit chip 14 to probe contacts 16A and 16B to provide impedance matching from the tissue medium through the probe contacts 16A and 16B and the impedance of the input of the integrated circuit chip 14. Matching circuit 29 is also operatively coupled to energy harvesting circuitry 20 and on-board electronic circuitry 22 at the output ends thereof. In the illustrated embodiment, on-board electronic circuitry 22 includes control circuitry 24, such as a microprocessor, a microcontroller or some other suitable custom control circuitry, along with an associated memory, and transmitter circuitry 26. In operation, energy harvesting circuitry 20 is structured to receive RF energy from RFID reader device 10 (via a touch probe in the manner described herein) and harvest energy therefrom by converting the received RE energy into DC energy, e.g., a DC voltage. The DC voltage is then used to power on-board electronic circuitry 22. Transmitter circuitry 26 is structured to transmit an RE information signal to RFID reader device 10 through probe contacts 16A and 16B.

In the particular embodiment shown in FIG. 2, energy harvesting circuitry 20 of integrated circuit chip 14 includes a matching network 28 electrically connected to matching circuit 29 for tissue and probe matching and then to probe contacts 16A and 16B. Matching network 28 is also electrically connected to a voltage boosting and rectifying circuit preferably in the form of a one or more stage charge pump 30. Charge pumps are well known in the art. Basically, one stage of a charge pump increases the effective amplitude of an AC input voltage with the resulting increased DC voltage appearing on an output capacitor or other appropriate circuit device. Successive stages of a charge pump, if present, will essentially increase the voltage from the previous stage resulting in an increased output voltage. In operation, probe contacts 16A and 16B receive RF energy that is provided by RFID reader device 10 as described herein. The received RF energy is provided, in the form of an AC signal, to charge pump 30 through matching circuit 29 and the associated matching network 28. Charge pump 30 rectifies the received AC signal to produce a DC signal that is amplified as compared to what it would have been had a simple rectifier been used. In the exemplary embodiment, matching circuit 29 and matching network 28 are chosen (i.e., their impedances are chosen) so as to maximize some criterion such as the voltage of the DC signal output by charge pump 30.

In one particular, non-limiting exemplary embodiment, RFID transponder device 8 may further include one or more sensors 27 operatively coupled to control circuitry 24. The function of such sensors 27 is to monitor medical implant device 4 by integrating such sensors 27 into RFID transponder device 8 to help monitor the status of medical implant device 4 and the tissue environment around medical implant device 4. More specifically, a major problem during the recovery period for orthopedic surgeries is the infection of the implant, an ill status difficult to observe and diagnose. Sensors 27 in the form of one or more of a temperature, pH, or microorganism sensor would be useful for reading a change in the temperature, level, and/or microorganism presence in order to determine whether medical implant device 4 is infected at an early stage. Other examples of biosensors that may be used for sensors 27 include pressure sensors, chemical sensors, and accelerometers.

Figure 3:
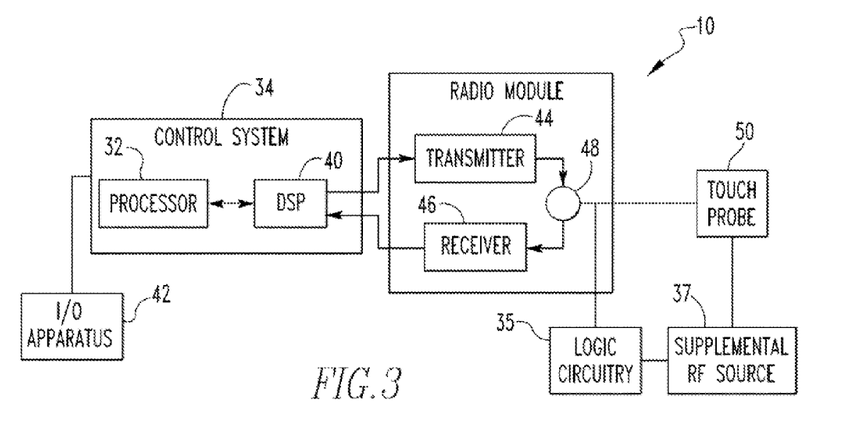
FIG. 3 is a schematic diagram of a touch probe type RFID reader device according to one non-limiting exemplary embodiment that may be used in the system of FIG. 1.

FIG. 3 is a schematic diagram of a touch probe type RFID reader device 10 according to one non-limiting exemplary embodiment of the present invention. As noted elsewhere herein and as described in detail below, touch probe type RFID reader device 10 is able to read information from and write information to RFID transponder device 8 by making a direct (i.e., non-air interface) electrical connection thereto RFID reader device 10 includes a control system 34, a primary radio module 36, logic circuitry 35, and a supplemental RF source 37, such as, without limitation, an RF oscillator. In various alternative embodiments, touch probe type RFID reader device 10 may form part of a mobile computing, device such as a smart phone, a tablet computer, a laptop computer, a smart watch, etc.

In the exemplary embodiment shown in FIG. 3, control system 34 includes a processor 38, such as a microcontroller or microprocessor, and a digital signal processor (DSP) 40 (which may be a DSP chip or any other circuit that provides the necessary ability to process digital signals), although other configurations are possible. Processor 38 provides control over high level operation of touch probe RFID reader device 10 and may communicate with an external network and/or peripheral devices such as, without limitation, an 110 apparatus 42 (which enables information to be input into and output from touch probe RFID reader device 10), 110 apparatus 42 may include a display, a keyboard, a touchscreen, or some combination thereof. DSP 40 provides direct control over all operations of radio module 36 in response to high level commands provided by processor 38, and processes data signals received from RFID transponder device 8 as described herein. Radio module 36 is adapted to provide for communications to/from RFID transponder device 10 by generating and receiving RF signals in the manner described herein.

More particularly, radio module 36 further comprises a transmitter portion 44, a receiver portion 46, and a hybrid 48. Hybrid 48 may further comprise a circulator. Transmitter portion 44 preferably includes a local oscillator that generates an RF carrier frequency. Transmitter portion 44 sends a transmission signal modulated by the RF carrier frequency to hybrid 48, which in turn passes the signal to a touch probe device 50. Hybrid 48 connects transmitter portion 44 and receiver portion 46 to touch probe device 50 while isolating them from each other. In particular, hybrid 48 allows a relatively strong signal to be sent from transmitter portion 44 while simultaneously receiving a weaker signal received from RFID transponder device 8. Touch probe device SO includes one or more electrical contacts or electrodes that are adapted to be selectively and temporarily mated and brought into electrical contact with probe contacts 16A and 16B of RFID transponder device 8. As such, the signals generated by touch probe type RFID reader device 10, that would in conventional RFID readers be sent over an air interface, may instead be directly transmitted (i.e., not over an air interface) to RFID transponder device 8 (e.g., through the living tissue of the patient), and thus integrated circuit chip 14 provided therein. Similarly, the signals generated by integrated circuit chip 14, that in a conventional configuration would have been sent via antenna over an air interface to an RFID reader, may instead he directly transmitted (i.e., not over an air interface) to RFID reader device 10 through touch probe device 50, In one particular embodiment, touch probe device 50 is a wand-like device having two conductors fixed at the end thereof with a center to center distance to accommodate the spacing of probe contacts 16A and 16B. In this embodiment, the wand-like touch probe device 50 is used to manually bring the conductors into electrical contact with probe contacts 16A and 16B through the tissue of patient 8 (i.e., transcutaneous contact) as needed.

The signals from RFID transponder device 8 transmitted through touch probe device 50 are passed back to hybrid 48, which forwards the signals to receiver portion 46. Receiver portion 46 mixes the captured signals with the RF carrier frequency generated by the local oscillator to directly downconvert the captured signals to a baseband information signal, which is provided to DSP 40 for processing thereby.

Referring again to FIG. 1, system 2 also includes a computing device 12, which may be, for example and without limitation, a PC (e.g., a Windows® based computer), a laptop computer, a tablet computer, a smartphone, or any other suitable device structured to perform the functionality described herein. Computing device 12 has internal storage and/or access to external storage through a network connection.

Figure 4:
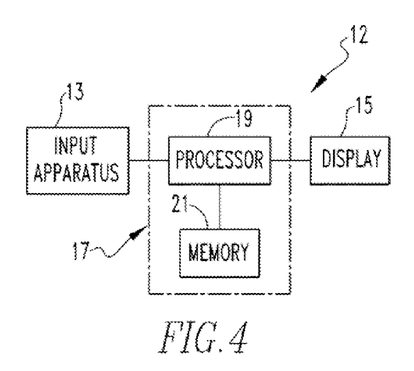
FIG. 4 is a block diagram of a computing device according to one exemplary embodiment that may be used in the system of FIG. 1.

FIG. 4 is a block diagram of computing device 12 according to one exemplary embodiment. As seen in FIG. 4, the exemplary computing device 12 is a PC and includes an input apparatus 13 (which in the illustrated embodiment is a keyboard), a display 15 (which in the illustrated embodiment is an LCD), and a processor apparatus 17. A user is able to provide input into processor apparatus 17 using input apparatus 13, and processor apparatus 17 provides output signals to display 15 to enable display 15 to display information to the user as described in detail herein. Processor apparatus 17 comprises a processor 19 and a memory 21. Processor 19 may be, for example and without limitation, a microprocessor (µP), a microcontroller, of some other suitable processing device, that interfaces with memory 21. Memory 21 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 21 has stored therein a number of routines that are executable by processor 19. One or more of the routines implement (by way of computer/processor executable instructions) at least portions of the method described in greater detail below (FIG. 4) for storing information on a medical implant device that identifies the particular elements of the medical implant device.

Figure 5:
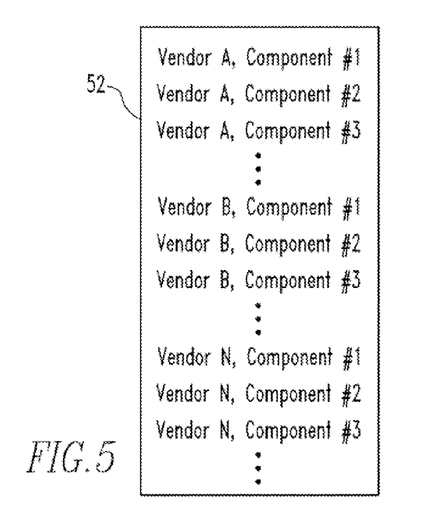
FIG. 5 is a schematic representation of implant element list data file according to the exemplary embodiment that may be used in the system of FIG. 1.

System 2 (FIG. 1) further includes an implant element list data file 52 that is accessible by computing device 12. For example, implant element list data file 52 may be stored on the internal storage of computing device 12 or may be stored in external storage (e.g., as part of a database component) accessible by computing device 12 through a network connection. FIG. 5 is a schematic representation of implant element list data file 52 according to the exemplary embodiment. As seen in FIG. 5, implant element list data file 52 comprises an extensive listing, by vendor and component/part number, of a plurality of implant elements that may be used in any of a number of different surgical procedures to form a medical implant device. System 2 still further includes patient medical record data files 54 and patient photograph data files 56 that are accessible by computing device 12. Like implant element list data file 52, patient medical record data files 54 and patient photograph data files 56 may be stored on the internal storage of computing device 12 or may be stored in external storage (e.g., as part of a database component) accessible by computing device 12 through a network connection. The function of implant element list data file 52, patient medical record data files 54 and patient photograph data files 56 is described in detail herein.

System 2 still further includes an x-ray machine 58 that is structured to capture digital x-ray images (e.g., in jpg or another suitable format) and communicate such images, via a wired or wireless connection, to computing device 12.

Finally, system 2 also includes a caregiver computing device 60, which may be, for example and without limitation, a PC (e.g., a Windows® based computer), a laptop computer, a tablet computer, a smartphone, or any other suitable device structured to perform the functionality described herein. In the exemplary embodiment, caregiver computing device 60 is similar in structure to computing device 12 (FIG. 4). As seen in FIG. 1, caregiver computing device 60 is structured to be operatively coupled (e.g., via a wired or wireless connection) to RFID reader device 10 so that information read from RFID transponder device S as described herein can be provided to caregiver computing device 60 and displayed thereby.

Operation of system 2 according to the exemplary embodiment will now be described. Such operation will be described in conjunction with the flowchart of FIG. 6, which shows a method of operating system 2 according to the exemplary embodiment. For purposes of this description, it is assumed that a patient is to have a surgical procedure wherein medical implant device 4 which includes implant elements 6 will be implanted into the patient's body. Also, for illustrative purposes, medical implant device 4 will, in the present example, be assumed to be an orthopedic implant having a number of plates and screws for treating a fractured bone of the patient.

Figure 6:
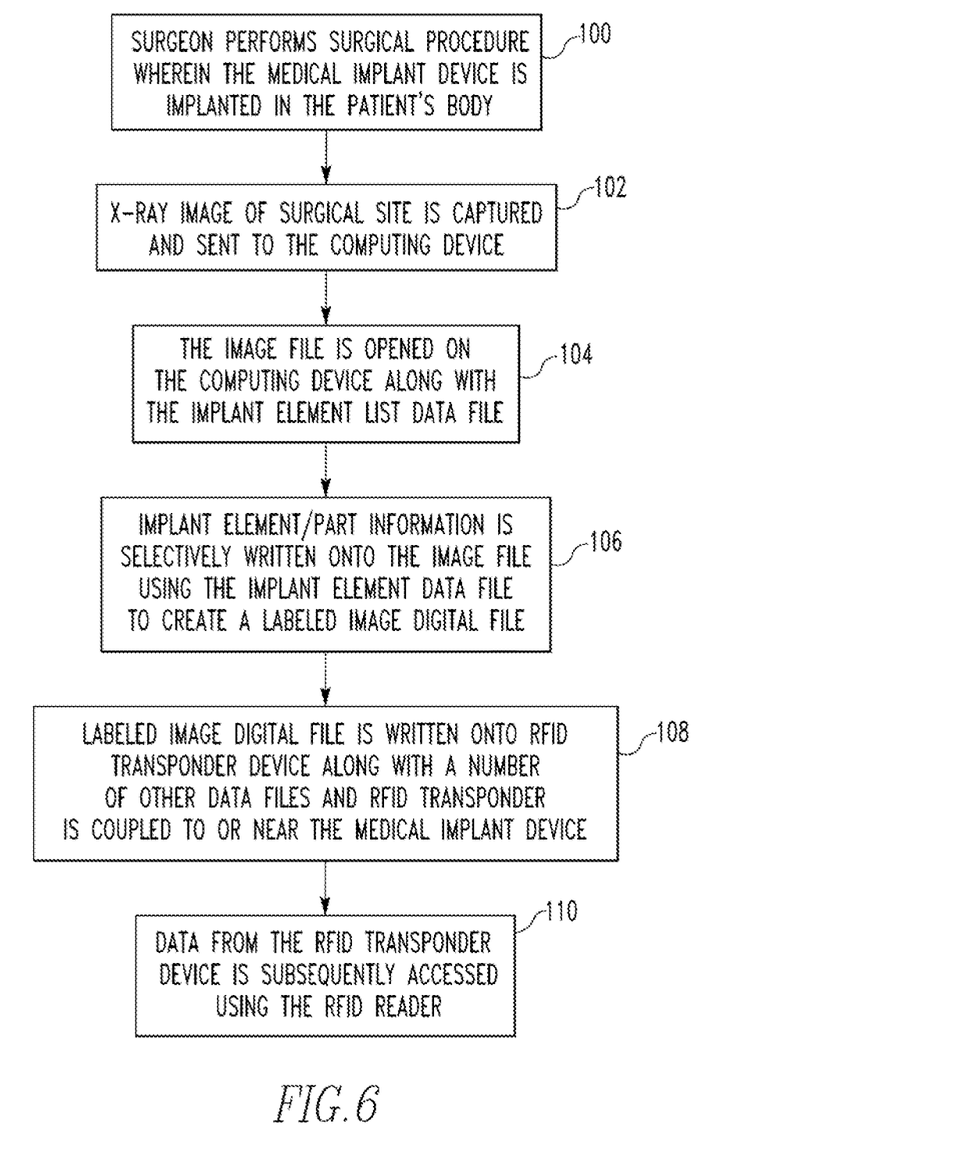
FIG. 6 is a flowchart which shows a method of operating the system of FIG. 1 according to the exemplary embodiment.
Figure 7:
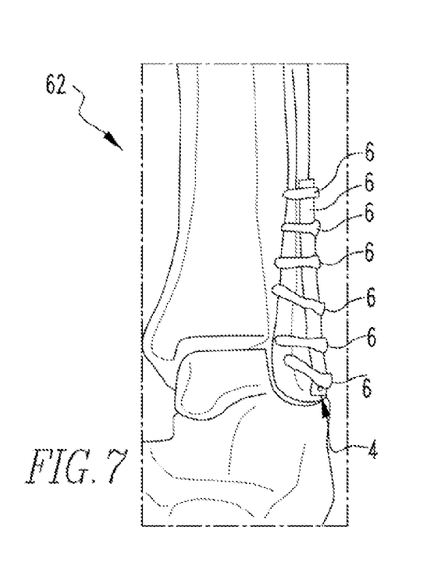
FIG. 7 is a schematic diagram of an exemplary X-ray image that may be employed in the system of FIG. 1.

Referring to FIG. 6, the method begins at step 100 with the surgeon performing the surgical procedure wherein medical implant device 4 is implanted into the patient's body. Next, at step 102, when the procedure is finished and before the surgical site is closed, an X-ray image 62 of the surgical site is captured and a digital file (e.g., in jpg format or some other suitable format) of the captured X-ray image 62 is sent to computing device 12. FIG. 7 shows an exemplary X-ray image 62 wherein medical implant device 4 including implant elements 6 can be readily seen.

Figure 8:
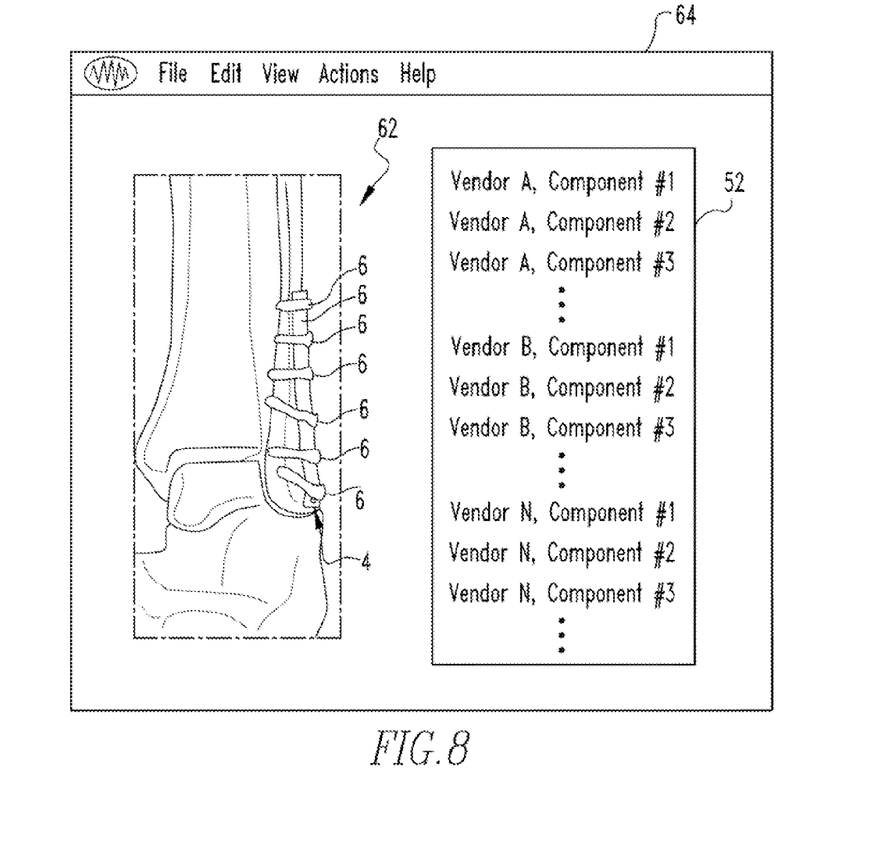
FIGS. 8-10 are schematic diagrams of exemplary display screen that may be employed in the system of FIG. 1.
Figure 9:
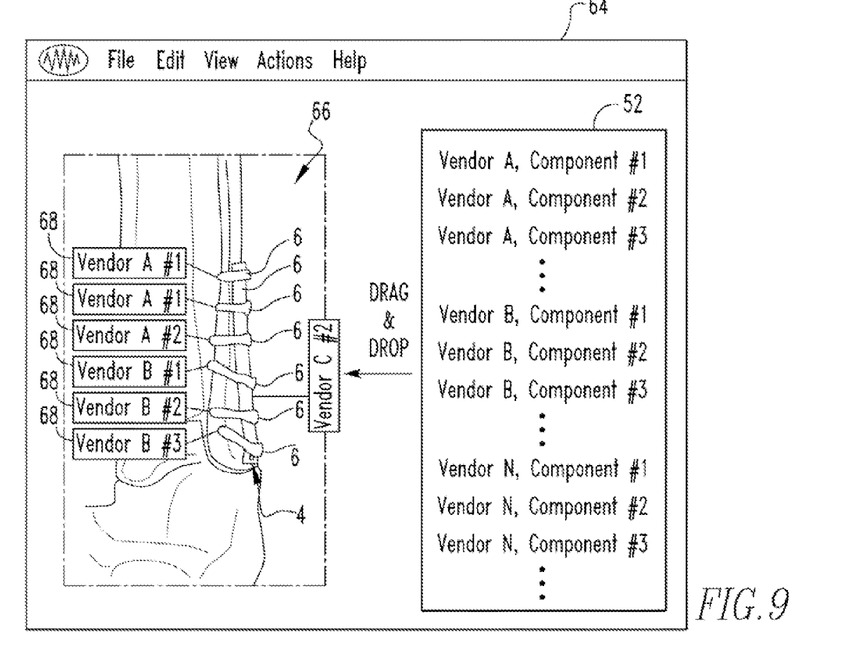

Then, at step 104, the surgeon or another caregiver working under the direction of the surgeon and using an application running on computing device 12 causes the digital. file containing the captured X-ray image 62 to be displayed on a display screen 64 of display 15 of computing device 12 along with implant element list data file 52 as shown in FIG. 8. Next, at step 106, implant element/part information identifying each of the implant elements 6 is selectively written onto the X-ray image 62 using implant element list data file 52 to create a labeled image 66 as shown in FIG. 9, Labeled image 66 is stored as a labeled image digital file by computing device 12. As seen in FIG. 9, a label 68 is provided in labeled image 66 adjacent each of the implant elements 6, wherein each label 68 includes information that identifies the associated implant element 6 (e.g., by vendor name and component/part 4). In the exemplary embodiment, the application running on computing device 12 is configured such that the implant element information identifying each of the implant elements 6 may be selectively written onto the X-ray image 62 in the appropriate location using a drag and drop functionality from implant element list data file 52. Alternatively, one skilled in the art would be able to use an alternative mechanism to transfer the labels 68 to labeled image 66. For example, information to be included in labeled image 66 may be input into computing device 12 using a bar code reader and associated database (e.g., to read manufacturer product barcodes) or an image scanner.

Once the labeled image 66 is completed, the method proceeds to step 108, wherein the labeled image digital file is written onto RFID transponder device 8 such that the labeled image digital file is stored in on-board electronic circuitry 22 of RFID transponder device 8. In the exemplary embodiment, this is done using RFID reader 10, computing device 12 and a suitable application run by computing device 12, such as, without limitation, the TegoDrive® software offered by Tego Inc. The TegoDrive® software is a software application wherein a tag (e.g., RFID transponder device 8) appears as a folder or drive within a PC or network (e.g., computing device 12) and wherein data (e.g., the labeled image digital file) can be saved directly from applications to the tag or added via drag and drop using RFID reader 10. In addition, a number of other data files may also optionally be written onto RFID transponder device 8 using RFID reader 10 and computing device 12. Such additional data files may include a patient electronic medical record 70 taken from patient medical record data files 54, a patient photograph 72 taken from patient photograph data files 56, or other data entered into computing device as described herein, such as a video image or a recordable audio image, among others. Also, in the exemplary embodiment, at step 108, once all of the desired data has been written onto RFID transponder device 8, RFID transponder device 8 is fixedly coupled to one of the implant elements 6 of medical implant device 4 using, for example, a suitable biocompatible adhesive, in an alternative embodiment, at step 108, once all of the desired data has been written onto RFID transponder device 8, RFID transponder device 8 is fixedly coupled to the patient's body or tissue using, for example, a suitable biocompatible suture or adhesive. The surgical site may then be closed.

Figure 10:
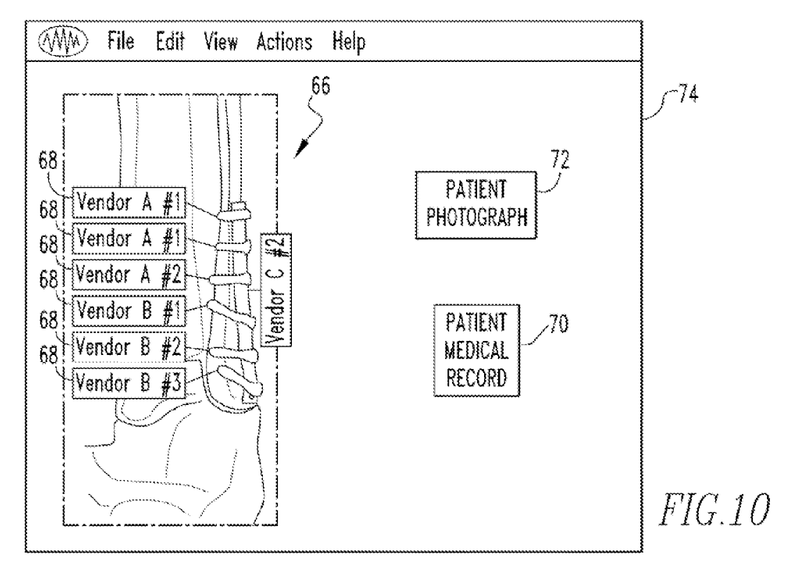

Thereafter, as seen in step 110, a caregiver, such as another surgeon, can access the data that has been written onto RFID transponder device 8 as needed using RFID reader 10 in the manner described herein. More specifically, if at a later time one or more of the implant elements 6 of medical implant device 4 need to be adjusted, repaired or replaced, the caregiver can cause the data that has been written onto RFID transponder device 8 to be accessed and displayed on a display screen 74 of caregiver computing device 60 as shown in FIG. 10. As a result, the caregiver will be able to readily identify each of the implant elements 6 of medical implant device 4 prior to any subsequent medical steps being performed. In addition, to the extent that they have also been written onto RFID transponder device 8 as described herein, the caregiver will also have ready access to patient electronic medical record 70 and/or patient photograph 72, in addition, the data on the RFID transponder device 8 may be updated (i.e., data is re-recorded) as required following the above procedure. For example, patient visit information, physiotherapy visit, information, and patient photos can be downloaded to RFID transponder device 8 as needed.

In the exemplary embodiment, system 2 is compatible with cloud memory storage systems. Furthermore, RFID reader 10 may be coupled to a computing device such as a laptop or tablet computer or smart phone so that information relating to medical implant device for can be downloaded to or uploaded from such a computing device.

In one non-limiting, exemplary embodiment, RFID transponder device 8 may be provided with encryption technology in order to protect the information stored therein.

Figure 11:
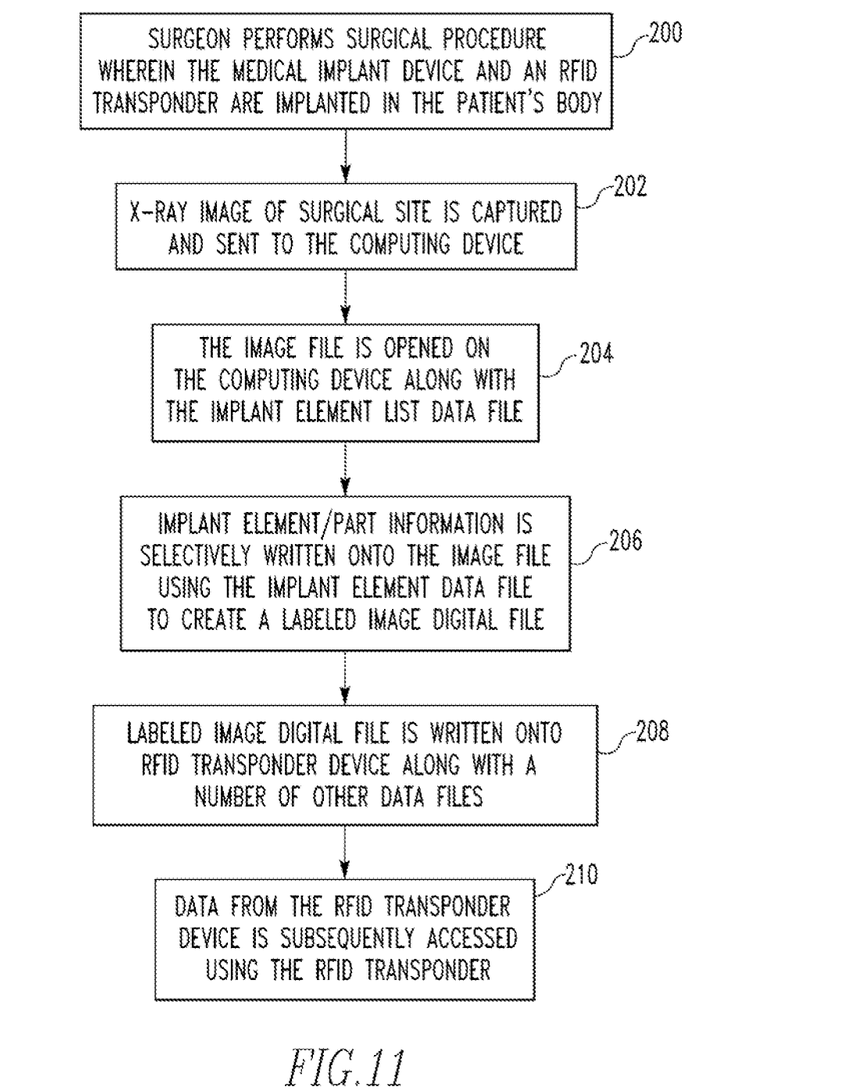
FIG. 11 is a flowchart which shows a method of operating the system of FIG. 1 according to an alternative exemplary embodiment.

FIG. 11 is a flowchart of an alternative method of operation of system 2 according to an additional exemplary embodiment. The method begins at step 200 with the surgeon performing the surgical procedure wherein medical implant device 4 is implanted into the patient's body along with RFID transponder device 8. RFID transponder device 8 may be fixedly coupled to one of the implant elements 6 of medical implant device 4 using, for example, a suitable biocompatible adhesive, or, alternatively, RFID transponder device 8 may be fixedly coupled to the patient's body or tissue using, for example, a suitable biocompatible suture or adhesive. Next, at step 202, when the procedure is finished and after or alternatively before) the surgical site is closed, an X-ray image 62 of the surgical site as described herein is captured and a digital file (e.g., in jpg format or some other suitable format) of the captured X-ray image 62 is sent to computing device 12.

Then, at step 204, the surgeon or another caregiver working under the direction of the surgeon and using an application running on computing device 12 causes the digital file containing the captured X-ray image 62 to be displayed on a display screen 64 of display 15 of computing device 12 along with implant element list data file 52 (FIG. 8). Next, at step 206, implant element/part information identifying each of the implant elements 6 is selectively written onto the X-ray image 62 using implant element list data file 52 to create a labeled image 66 (FIG, 9). Labeled image 66 is stored as a labeled image digital file by computing device 12. Once the labeled image 66 is completed, the method proceeds to step 208, wherein the labeled image digital file is written onto RFID transponder device 8 (that is inside or otherwise attached (e.g., outside) the patient's body) such that the labeled image digital file is stored in on-board electronic circuitry 22 of RFID transponder device 8. In the exemplary embodiment, this is done using touch probe type RFID reader 10 and computing device 12 as described herein. In addition, a number of other data files may also optionally be written onto RFID transponder device 8 using RFID reader 10 and computing device 12. Such additional data files may include a patient electronic medical record 70 taken from patient medical record data files 54 and a patient photograph 72 taken from patient photograph data files 56. Thereafter, as seen in step 210, a caregiver, such as another surgeon, can access the data that has been written onto RFID transponder device 8 as needed using RFID reader 10 in the manner described herein.

System 2 described herein is compatible with and can interact with electronic medical record systems (EMR) and/or medical device registries, such as hip and knee, cardiac, breast implant, and organ transplant registries.

Moreover, while in the exemplary embodiment system to employees and RFID transponder device 8, that device may take other forms such as without limitation, a Bluetooth-based transponder device.

In the claims, any reference signs placed between parentheses shall riot be construed as limiting the claim. The word "comprising" or "including" does not exclude the presence of elements or steps other than those listed in a claim. In a device claim enumerating several means, several of these means may he embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of storing information relating to a medical implant device having a number of implant elements, comprising:
   receiving a first image, the first image showing a surgical site and the medical implant device;
   creating a second image using the first image and a stored list of possible implant elements, the second image showing the surgical site and the medical implant device with a number of labels associated therewith, wherein each of the labels is associated with a respective one of the implant elements and indicates one of the possible implant elements from the stored list; and
   storing the second image on a transponder device structured to be attached to the medical implant device or at a medically appropriate site on or within a patient's body.

2. The method according to claim 1, wherein the transponder device is an RFID transponder device.

3. The method according to claim 1, further comprising storing a number of additional data files on the transponder device.

4. The method according to claim 1, wherein the additional data files include a medical record of a patient receiving the medical implant device.

5. The method according to claim 1, wherein the additional data files include a photograph of a patient receiving the medical implant device.

6. The method according to claim 1, further comprising fixedly coupling the transponder device storing the second image to the medical implant device or the medically appropriate site within the patient's body.

7. The method according to claim 1, further comprising accessing the second image from the transponder device and displaying the second image.

8. The method according to claim 1, wherein the first image is an X-ray image.

9. The method according to claim 1, wherein each label is positioned immediately adjacent to the one of the implant elements with which it is associated.

10. The method according to claim 1, wherein the list of possible implant elements identifies for each possible implant element a vendor of the possible implant element and an identifier for the possible implant element.

11. The method according to claim 1, wherein the transponder device includes a sensor structured to monitor a status of the medical implant device or a tissue environment surrounding the medical implant device.

12. The computer program product, comprising a computer usable non-transitory medium having a computer readable program code embodied therein, the computer readable program code having a number of routines adapted to be executed to implement a method for storing information relating to a medical implant device having a number of implant elements, the number of routines being adapted to:
   receive a first image, the first image showing a surgical site and the medical implant device,
   create a second image using the first image and a stored list of possible implant elements, the second image showing the surgical site and the medical implant device with a number of labels associated therewith, wherein each of the labels is associated with a respective one of the implant elements and indicates one of the possible implant elements from the stored list; and
   cause the second image to be stored on an transponder device structured to be attached to the medical implant device or at a medically appropriate site on or within a patient's body.

13. The computer program product according to claim 12, the number of routines being further adapted to store a number of additional data files on the transponder device.

14. The computer program product according to claim 13, wherein the additional data files include a medical record of a patient receiving the medical implant device.

15. The computer program product according to claim 13, wherein the additional data files include a photograph of a patient receiving the medical implant device.

16. The computer program product according to claim 12, wherein the first image is an X-ray image.

17. The computer program product according to claim 12, wherein each label is positioned immediately adjacent to the one of the implant elements with which it is associated.

18. The computer program product according to claim 12, wherein the list of possible implant elements identifies for each possible implant element a vendor of the possible implant element and an identifier for the possible implant element.

19. A system for storing information relating to a medical implant device having a number of implant elements, comprising:
   an image receiving component structured and configured for receiving a first image, the first image showing a surgical site and the medical implant device;
   a storage component structured and configured for storing a stored list of possible implant elements;

an image creating component structured and configured for creating a second image using the first image and the stored list, of possible implant elements, the second image showing the surgical site and the medical implant, device with a number of labels associated therewith, wherein each of the labels is associated with a respective one of the implant elements and indicates one of the possible implant elements from the stored list; and a transponder storage component structured and configured for storing the second image on a transponder device structured to be attached to the medical implant device or at a medically appropriate site on or within a patient's body.

20. The system according to claim 19, wherein the transponder device is an RFID transponder device.

21. The system according to claim 19, the image creating component being structured and configured for storing a number of additional data files on the transponder device.

22. The system according to claim 21, wherein the additional data files include a medical record of a patient receiving the medical implant device.

23. The system according to claim 21, wherein the additional data files include a photograph of a patient receiving the medical implant device.

24. The system according to claim 19, wherein the first image is an X-ray image.

25. The system according, to claim 19, wherein each label is positioned immediately adjacent to the one of the implant elements with which it is associated.

26. The system according to claim 19, wherein the list of possible implant elements identifies for each possible implant element a vendor of the possible implant element and an identifier for the possible implant element.

27. The system according to claim 19, wherein the transponder device includes a sensor structured to monitor a status of the medical implant device or a tissue environment surrounding the medical implant device.

28. The method according to claim 1, wherein the transponder device is structured to be attached at a medically appropriate site on the patient's body on or in an object that can be worn on or embedded on the patient's body.

* * * * *